US00PP37003P2

(12) United States Plant Patent
Smith

(10) Patent No.: US PP37,003 P2
(45) Date of Patent: Oct. 7, 2025

(54) ***PAEONIA* PLANT NAMED 'Smithopus5'**

(50) Latin Name: ***Paeonia* hybrid**
Varietal Denomination: Smithopus5

(71) Applicant: Donald R. Smith, Fairfield, CT (US)

(72) Inventor: Donald R. Smith, Fairfield, CT (US)

( * ) Notice: Subject to any disclaimer, the term of this patent is extended or adjusted under 35 U.S.C. 154(b) by 0 days.

(21) Appl. No.: 18/966,383

(22) Filed: Dec. 3, 2024

(51) Int. Cl.
*A01H 5/02* (2018.01)
*A01H 6/00* (2018.01)

(52) U.S. Cl.
USPC ..... Plt./316

(58) Field of Classification Search
USPC ..... Plt./316
CPC ..... A01H 5/02; A01H 5/00; A01H 6/00
See application file for complete search history.

(56) References Cited

PUBLICATIONS

Plants Nouveau 2025 Garden Candy Itoh Peonies retrieved on Feb. 27, 2025 at https://www.plantsnouveau.com/collections/garden-candy, 11 pp. (Year: 2025).*

* cited by examiner

*Primary Examiner* — June Hwu
(74) *Attorney, Agent, or Firm* — Cassandra Bright

(57) ABSTRACT

A new and distinct cultivar of intersectional hybrid (Itoh) *Paeonia* plant named 'Smithopus5' is disclosed, large peach colored flowers of double form carried on strong stems, which present the flowers above and beyond the foliage. Plants have very attractive, dissected foliage, which lasts through the fall and is also highly disease resistant. Plants have a symmetrical, compact plant habit/shape which is excellent in the landscape. The new variety is a intersectional hybrid (Itoh) *Paeonia* normally produced as an outdoor ornamental garden plant.

2 Drawing Sheets

Figure 1:
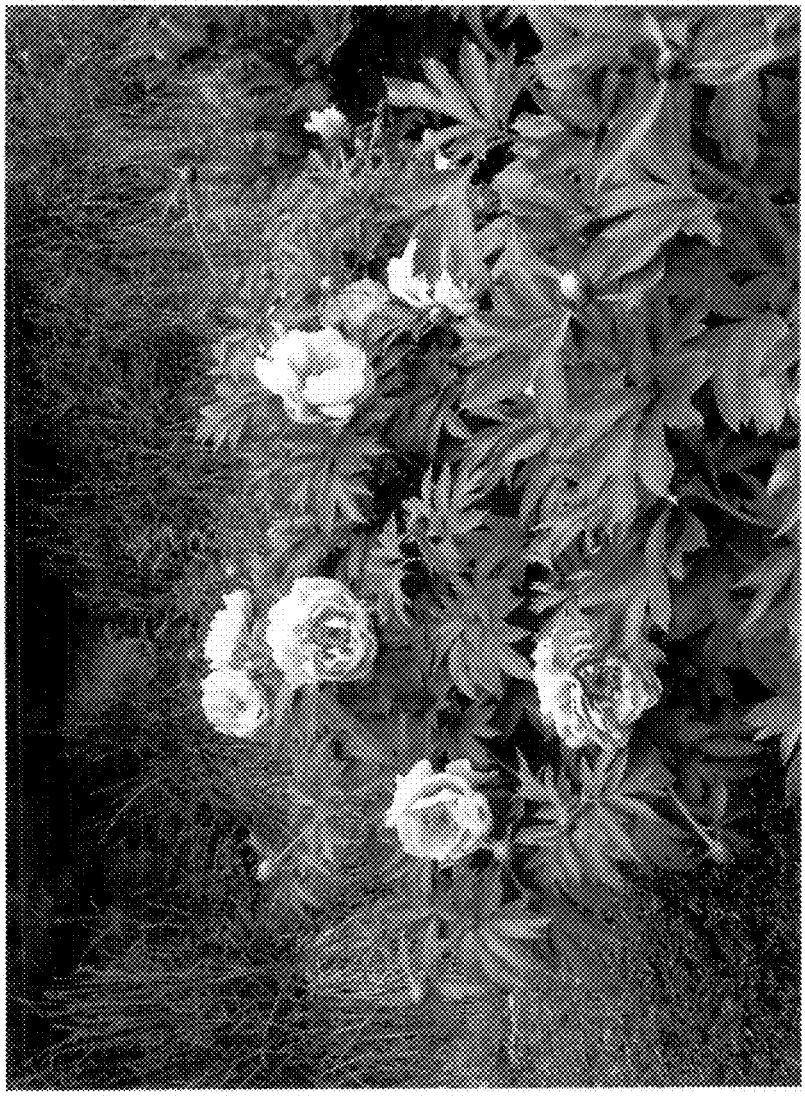

Latin name of the genus and species: *Paeonia* hybrid.
Variety denomination: 'Smithopus5'.

BACKGROUND OF THE INVENTION

The new cultivar is a product of a planned breeding program conducted by the inventor to produce new *Paeonia* hybrid cultivars with strong stems, large panicles, and compact habits. The crossing resulting in the new cultivar was made in summer of 2002 in a backyard in Windham, NH.

The seed parent is the cultivar *Paeonia* 'Martha W', unpatented. The pollen parent is the cultivar *Paeonia* 'Golden Experience', unpatented. The new cultivar was found and selected by the inventor in 2012 in the same backyard in Windham, NH. Asexual reproduction of the new cultivar 'Smithopus5' was first performed at a research laboratory during 2018 in Heerhugowaard, the Netherlands by tissue culture. Through subsequent confidential propagation, multiple additional generations have been reproduced, having shown that the unique features of this cultivar are stable and reproduced true to type.

Plants of the new cultivar were first sold Jul. 1, 2024 in the United States. This was from plant material originating from the inventor. Plants were advertised on a website from the Entity "Plants Nouveau", which has received a license, information and plant material directly from the inventor.

SUMMARY OF THE INVENTION

The cultivar 'Smithopus5' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Smithopus5'. These characteristics in combination distinguish 'Smithopus5' as a new and distinct *Paeonia* cultivar:

1. New cultivar is an intersectional hybrid (Itoh) peony from a cross of an herbaceous peony (lactiflora) with a hybrid tree peony.
2. It is a sterile first-generation hybrid with triploid (3n) ploidy level.
3. New cultivar has large peach colored flowers of fully double form carried on strong stems, which present the flowers above and beyond the foliage.
4. New cultivar has very attractive, dissected foliage, which lasts through the fall and is also observed disease resistant.
5. New cultivar has a symmetrical, compact plant habit/shape and makes an ideal landscape plant.

PARENT COMPARISONS

Plants of 'Smithopus5' are similar to plants of the seed parent in most horticultural characteristics, however, plants of 'Smithopus5' differ in the following:

1. Seed parent has fully herbaceous stems and growth habit, whereas the new cultivar has stronger semi-woody to woody stems and many above-ground buds, yet grows primarily as an herbaceous plant.
2. Seed parent has pink flowers of single form with 11-13 petals, whereas the new cultivar has double flowers peach colored flowers with many more petals (about 30 to 40).
3. Seed parent blooms 1-2 weeks later than the new cultivar.

4. Seed parent has many lateral flowers per stem, whereas the new cultivar has only 1 or 2.
5. Seed parent is highly fertile both ways, whereas the new cultivar is a sterile triploid.

Plants of 'Smithopus5' are similar to plants of the pollen parent in most horticultural characteristics, however, plants of 'Smithopus5' differ in the following:

1. The new variety has peach colored flowers whereas 'Golden Experience' has bright yellow flowers.
2. The new variety has double flowers whereas 'Golden Experience' has flowers with single to semi-double form.
3. Pollen parent is a woody tree peony hybrid that has winter hardy, woody stems, whereas the new variety has herbaceous stems that are much less winter hardy.
4. Pollen parent has more upright, shrub-like plant and growth habit, whereas the new variety has mostly herbaceous habit.
5. Pollen parent blooms 1-2 weeks before the new variety.

COMMERCIAL COMPARISON

Plants of 'Smithopus5' can be compared to plants of the commercial cultivar *Paeonia* intersectional hybrid 'Magical Mystery Tour', unpatented. Plants of 'Smithopus5' are similar to plants of 'Magical Mystery Tour' in most horticultural characteristics, however, plants of 'Smithopus5' differ in the following:

1. 'Magical Mystery Tour' has peach/pink colored flowers which are more pink in their mature stage, whereas 'Smithopus5' is colored an orange-peach in it's mature stage.
2. Flowers of 'Smithopus5' are more double than flowers of 'Magical Mystery Tour'.
3. 'Smithopus5' is more floriferous than 'Magical Mystery Tour'.

Plants of 'Smithopus5' can be compared to plants of the commercial cultivar *Paeonia* intersectional hybrid 'Garden Treasure', unpatented. Plants of 'Smithopus5' are similar to plants of 'Garden Treasure' in most horticultural characteristics, however, plants of 'Smithopus5' differ in the following:

1. 'Garden Treasure' has yellow flower petals with prominent red basal flares, whereas the new variety has peach colored flowers and a nearly non-visible red-purple basal blotch.
2. 'Garden Treasure' is shorter in height than the new variety

BRIEF DESCRIPTION OF THE PHOTOGRAPHS

The accompanying photograph in FIG. 1 illustrates in full color a typical plant of 'Smithopus5' grown in a field in Fairfield, CT. This plant is approximately 3 years old.

Figure 2:
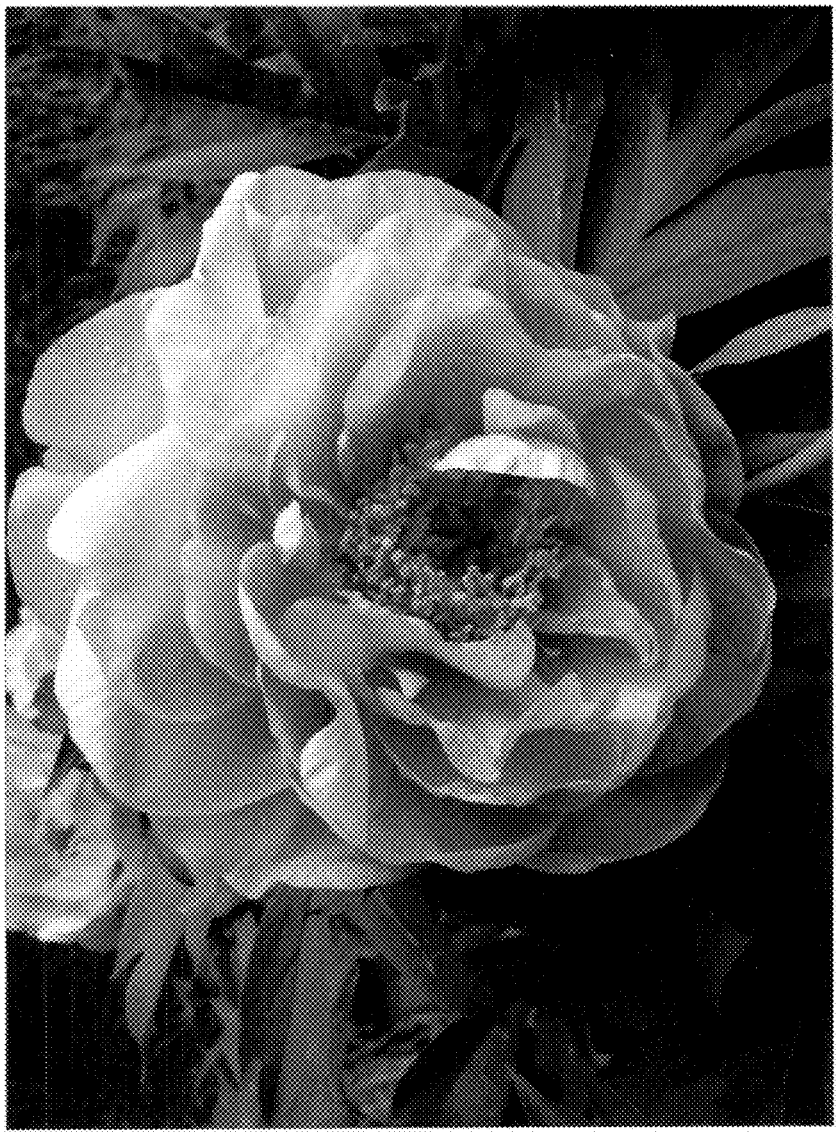

FIG. 2 illustrates in full color a close-up of a mature flower of 'Smithopus5'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'Smithopus5' plants grown outdoors in Camarillo, CA. The plants were 2 to 3 years old from large tubers, grown in 5-gallon pots. Temperatures ranged from 5° C. to 10° C. at night to 12° C. to 30° C. during the day. No artificial light, photoperiodic treatments were given to the plants. Measurements and numerical values represent averages of typical plant types.

Botanical classification: *Paeonia* hybrid 'Smithopus5'.

PROPAGATION

Typically by shoot tissue culture.

Root description: Freely branching storage root with numerous feeder roots. Roots various shades of tan and brown, not accurately measured with a color chart.

Tubers: Elongated, typically 4 to 10 cm long and 2 to 4 cm in diameter. Colored near Greyed-Orange 166C.

PLANT

Growth habit: Vigorous perennial herbaceous shrub. Semi-upright growth habit.

Height: Approximately 60 to 70 cm at opening of first flower.

Plant spread: Approximately 70 cm.

Stems:

Length: Approximately 40 to 55 cm.

Diameter: Average range 8 to 10 mm.

Strength: Strong.

Internode length: 5 to 7 cm, highly variable.

Color: Near RHS Yellow-Green 145A.

Texture: Glabrous.

Age of plant described: Approximately 2 to 3 years.

FOLIAGE

Leaf: Alternate, pinnate compound, with an overall circular to ovate shape, which is slightly wider than long. Average fully expanded leaf 18 cm long and 25 cm wide, excluding the petiole. Horizontal to semi-erect attitude.

Primary leaflets:

*Shape*.—Obovate.

*Quantity and arrangement*.—3 primary leaflets further divided into 3 to 5 deeply divided secondary leaflets. All leaflets sessile.

*Length*.—Average range 8 to 10 cm.

*Width*.—Average range 11 to 16 cm.

Individual primary leaflet blades:

*Shape of blade*.—Broad ovate, variably incised.

*Apex*.—Acute.

*Base*.—Attenuate.

*Margin*.—Deeply incised.

*Texture of top surface*.—Glabrous.

*Texture of bottom surface*.—Glabrous.

*Appearance of top surface*.—Matte.

*Appearance of bottom surface*.—Matte.

*Aspect*.—Flat to very slightly reflexed downward.

Individual secondary leaflet blades:

*Shape of blade*.—Oblanceolate, variably incised.

*Apex*.—Acute.

*Base*.—Attenuate.

*Margin*.—Deeply incised.

*Texture of top surface*.—Glabrous.

*Texture of bottom surface*.—Glabrous.

*Appearance of top surface*.—Matte.

*Appearance of bottom surface*.—Matte.
*Aspect*.—Flat to very minutely reflexed downward.
*Color*.—Emerging — Upper side: Near RHS Green 138B. Under side: Near RHS Green 138C. Young — Upper side: Near RHS Green 137D. Under side: Near RHS Green 138A. Mature — Upper side: Near RHS Green 137B. Under side: Near RHS Green 138A.
*Venation*.—Type: Pinnate. Venation color upper side: Near RHS Yellow-Green N144D. Venation color under side: Near RHS Yellow-Green 145B.
*Petiole*.—Length: Average 10 cm. Diameter: 5 to 6 mm. Color: Near RHS Yellow-Green 145A. Texture: Glabrous.

FLOWER

Natural flowering season: Flowering begins late April in Southern California. Flowering extends throughout the Summer, depending on environmental conditions.
Inflorescence type and habit: Double form with conspicuous stamens. 3 to 4 loose whorls. Shape regularly round. Erect flower attitude.
Flower longevity on plant: Approximately 10 days on the plant. Varies considerably with environmental conditions.
Quantity of flowers: 1 to 2 per stem. 5 to 9 flowering stems per plant.
Flower size:
*Diameter*.—Approximately 14 cm.
*Depth*.—Approximately 7 cm. (Flower height).
Peduncle:
*Length*.—Approximately 10 cm.
*Diameter*.—Approximately 5 mm.
*Color*.—Near RHS Yellow-Green 145A.
*Strength*.—Strong.
*Texture*.—Glabrous.
Petals:
*Petal arrangement*.—3 to 4 loose whorls of about 10 to 12 petals per whorl.
*Size*.—Length: Average 6.5 cm. Width: Average 5 cm.
*Shape*.—Obovate.
*Margin*.—Entire.
*Apex*.—Emarginate.
*Base*.—Broad attenuate.
*Texture*.—Smooth, glabrous all surfaces.
*Aspect*.—Moderately reflexed downward.
Color:
*Petals*.—When opening: Opening: Upper surface: Near RHS Yellow-Orange 20C flushed near veins Red-Purple 71A. Large basal blotch near 71A. Blotch about 1.5 cm in length and 2 cm in width. Near RHS Orange 24D flushed near veins Red-Purple 60A. Large basal blotch near Red-Purple 59A. Blotch about 1.5 cm in length and 2 cm in width. Lower surface: Fully opened: Upper surface: Near RHS Orange-Red 35C suffused with Red-Purple 59B. Large basal blotch near Red-Purple 71A. Blotch about 1.9 cm in length and 2.3 cm in width. Lower surface: Near RHS Orange-Red 35D suffused with Red-Purple 59A. Large basal blotch near Red-Purple 60A. Blotch about 1.9 cm in length and 2.3 cm in width.
Petaloids: Not present.
Bud:
*Shape*.—Oblate.
*Length*.—Approximately 2 cm.
Diameter.—Approximately 2.8 cm.
*Color*.—Near RHS Yellow-Green 145A flushed Red-Purple 60A.
Sepals:
*Quantity*.—2 to 4.
*Length*.—2 to 3.5 cm.
*Width*.—2 cm.
*Shape*.—Deltate.
*Aspect*.—Flat.
*Attitude*.—Horizontal.
*Apex*.—Acute.
*Base*.—Truncate.
*Margin*.—Entire.
*Color*.—Interior Surface: RHS Green 137D. Exterior Surface: RHS Green 137D.
*Texture*.—Glabrous.
Fragrance: Light, honeylike.

REPRODUCTIVE ORGANS

Androecium:
Stamens:
*Quantity*.—80 to 100.
*Length*.—15 to 20 mm.
*Color*.—Yellow 9D, center section Red-Purple 61B.
Anthers:
*Shape*.—Linear or curled.
*Length*.—3 to 4 mm.
*Color*.—Yellow 5A.
Gynoecium:
Pistil:
*Type*.—Compound. Petaloid, stigma only.
*Number*.—3.
*Carpel length*.—1.8 cm.
*Carpel width*.—1.4 cm.
*Carpel pubescence*.—Dense.
*Openness of disc*.—Partly open.
*Stigma*.—Partly Petaloid. 5 mm long and 4 mm in diameter. Shape Petaloid section: Irregular circular. Color: Near RHS Red-Purple 61A.
*Ovary color*.—Near RHS Yellow-Green 145C.

OTHER CHARACTERISTICS

Disease and pest resistance: Observed resistance to foliar diseases of *Paeonia*. Typical foliar diseases of *Paeonia* include *Botrytis paeoniae, Graphiopsis chlorocephala* and *Phytophthora*. sp. No additional resistance nor susceptibility to the normal diseases and pests of *Paeonia* has been observed.
Temperature tolerance: Typically USDA Zones 3 to 8.
Fruit/seed production: Not observed.

What is claimed is:

1. A new and distinct cultivar of *Paeonia* plant named 'Smithopus5' as herein illustrated and described.

* * * * *